United States Patent [19]

Hoffmann et al.

[11] 4,053,511
[45] Oct. 11, 1977

[54] NOPINYLAMINES

[75] Inventors: Werner Hoffmann, Neuhofen; Norbert Mueller, Mutterstadt; Joachim Paust, Neuhofen, all of Germany

[73] Assignee: BASF Aktiengesellschaft, Ludwigshafen, Germany

[21] Appl. No.: 728,528

[22] Filed: Oct. 1, 1976

[30] Foreign Application Priority Data

Oct. 11, 1975 Germany ............................ 2545657

[51] Int. Cl.² ...................... C07C 85/00; C07C 87/00
[52] U.S. Cl. ................................................ 260/563 P
[58] Field of Search ..................................... 260/563 P

[56] References Cited
U.S. PATENT DOCUMENTS

| | | | |
|---|---|---|---|
| 3,467,705 | 9/1969 | Gigante et al. | 260/563 P X |
| 3,483,254 | 12/1969 | Shen et al. | 260/563 P |
| 3,873,621 | 3/1975 | Kreevoy et al. | 260/563 P X |

Primary Examiner—Paul F. Shaver
Attorney, Agent, or Firm—Keil, Thompson & Shurtleff

[57] ABSTRACT

The nopinylamines of the general formula I

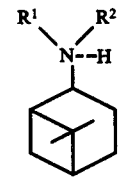

where $R^1$ and $R^2$ are hydrogen or alkyl of 1 to 5 carbon atoms, and the salts of these amines with mineral acids and with alkylcarboxylic acids of 1 to 4 carbon atoms.

The manufacture of I from nopinone (II)

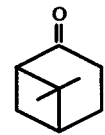

by aminating hydrogenation with amines (III)

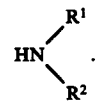

The use of I for resolving racemates of acid or acid-forming compounds, especially of DL-pantolactone.

2 Claims, No Drawings

NOPINYLAMINES

The present invention relates to nopinylamines of the general formula I

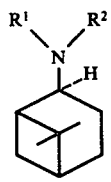

where $R^1$ and $R^2$ are hydrogen or alkyl of 1 to 5 carbon atoms, and to the salts of these amines with mineral acids and with alkylcarboxylic acids of 1 to 4 carbon atoms.

The invention also relates to the manufacture of these compounds and to their use for resolving racemates, above all for resolving racemic pantolactone. As is well known, pantolactone

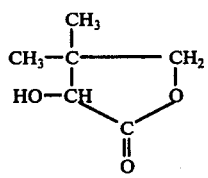

is the precursor for pantothenic acid (an extremely important compound in human and animal physiology), the β-alanide of pantoic acid, on which pantolactone is based. Since however only the D-form of pantothenic acid is physiologically active, it is necessary to manufacture this enantiomer or its precursor, pantolactone, in an optically pure form. This can be done, in principle, by the methods of resolution of the racemate, but this presupposes that the reagent used for the resolution is itself in an optically pure form. The use of natural compounds such as quinine (U.S. Pat. No. 2,319,545) or dehydroabietylamine (German Pat. No. 1,568,755) as reagents for the resolution is expensive and suffers from the further disadvantage that they themselves can only be re-purified by recrystallization.

The situation is similar when L-(+)-1-(4-nitrophenyl)-2-aminopropane-1,3-diol is used as a synthetic reagent for resolution (East German Pat. No. 32,628).

It is an object of the present invention to provide new, readily accessible reagents for the resolution of racemates, above all for the resolution of racemic pantolactone, which reagents can, in particular, also be regenerated by distillation.

We have found that this object is achieved by providing nopinylamines of the general formula I

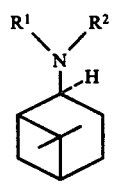

where $R^1$ and $R^2$ are hydrogen or alkyl of 1 to 5 carbon atoms, and the salts of these amines with mineral acids and with alkylcarboxylic acids of 1 to 4 carbon atoms, which nopinylamines and salts are exceptionally suitable for the resolution of racemates.

Further, it has been found that these compounds are obtained when nopinone (II)

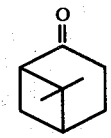

and an amine of the general formula III

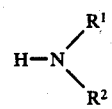

are conjointly subjected to aminating hydrogenation at from 50° to 200° C and, if desired, the resulting amines are converted to their salts, defined above.

It is remarkable that contrary to expectations it is not a mixture of

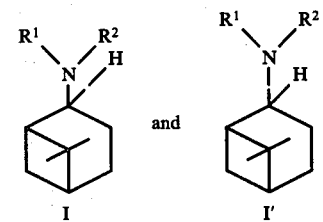

which is obtained, but the enantiomer I in a virtually pure form. It should be noted that, to understand the formula, the 2,4-endo bridge is to be visualized as being above the plane of the paper, whilst the bond shown in broken lines points below the plane of the paper.

Nopinone II is readily obtainable by ozonolysis of β-pinene, a natural compound available in adequate quantities. Reference may be made, for example, to the synthesis described in Comp. rend. 250 (1960), 1,078 – 1,080.

Amongst the starting compounds III, ammonia is the most important. However, from the point of view of resolution of racemates, primary amines such as methylamine, ethylamine, n-propylamine and isopropylamine and the remaining primary amines which accord with the above definition may also be used as starting compounds. The substituted amines are at times of importance if it is desired to increase the physical differences, in respect of solubility, of the diastereomers to be separated in the course of the racemate resolution process. For the resolution of pantolactone, unsubstituted nopinylamine I gives technically and economically the best results.

From our observations to date, the success of the process of the invention, i.e. the substantially exclusive formation of the enantiomer I, is independent of the process conditions used for the aminating hydrogenation, provided the stated temperature range is adhered to. At lower temperatures, the reaction takes place too slowly for technical purposes whilst at higher temperatures undesirable isomerization reactions take place.

The aminating hydrogenation is advantageously carried out with hydrogen under a pressure of from 1 to 300 bars, preferably from 80 to 200 bars, at from 50° to 150° C. Examples of suitable catalysts are finely divided platinum or palladium in the pure form or in the form of supported catalysts, but Raney nickel or Raney cobalt perform just as well and from an economic point of view are even preferable. It is advantageous to use the ammonia or amine III in from 10-fold to 20-fold molar excess in order to repress the hydrogenation to give nopinol. The presence of a solvent is not essential but is advantageous, in repressing the formation of by-products. Suitable solvents are, above all, volatile liquids such as methanol, ethanol, ether, ethyl acetate and benzene. The aminating hydrogenation can be carried out in one stage or, in the case of higher amines, in two separate steps, i.e. first the formation of the Schiff base, and then the hydrogenation.

The reaction mixtures may be worked up in the conventional manner, e.g. by removing the solvent and the amine by distillation and rectifying the residue which in the main consists of I. The free bases may be converted to their salts, e.g. hydrochlorides, sulfates, bisulfates, formates, acetates, propionates and butyrates, by conventional methods.

The compounds I, expecially (−)-nopinylamine, are outstandingly suitable for use in resolving racemates of acid or acid-forming compounds. Above all, racemic pantolactone forms, with nopinylamine, a pair of diastereomeric salts (nopinylammonium pantoates) which differ significantly in their solubility in water-soluble alkanols, water and mixtures of these media. The differences in solubility can be varied by adding other water-soluble solvents, e.g. acetone or dimethylformamide. For economic reasons, water is the preferred crystallization medium.

In general, the procedure followed is that racemic pantolactone is saponified with stoichiometric amounts of alkali metal hydroxide, e.g. sodium hydroxide or potassium hydroxide, in aqueous solution to give the corresponding racemic pantoate. The concentration of the pantoates in the aqueous solution is then brought to from 30 to 70% by weight, especially from 50 to 60% by weight (solution A).

The nopinylamine is preferably employed in the form of an aqueous solution, of from 20 to 50% strength, of its hydrochloride or bisulfate (solution B).

Solutions A and B are then mixed, in about equimolar ratios of their organic constituents, at from 20° to 60° C, preferably from 45 to 55° C, and the mixture is then allowed to cool at a rate of from 0.5 to 2° C/minute, to from about 20° to 5° C. Hereupon - if necessary assisted by a seed crystal - the crude (−)-nopinylamine salt of L-pantoic acid precipitates, in from 75 to 95% yield, as the less soluble diastereomer.

This salt, and the solution which remains (solution C) are then worked up by conventional methods. The salt is decomposed with, for example, sodium hydroxide solution, whereupon nopinylamine separates out. After extraction with ether, and passing in hydrogen chloride or adding sulfuric acid, the base, in the form of the hydrochloride or bisulfate, can be recycled. The amounts of material lost are insignificant. The aqueous sodium L-pantoate solution which remains can be racemized by conventional methods and then recycled to the process.

Solution C, containing the desired pantoic acid salt is rendered slightly alkaline, after which the nopinylamine is separated off by conventional methods. The solution is then acidified to about pH 1, preferably with sulfuric acid, whereupon D-(−)-pantolactone is reformed. The latter is extracted, for example with methylene chloride, and is isolated in the pure form by conventional methods.

A particularly advantageous embodiment of this process for resolving the racemate is to use the nopinylamine in only from 50 to 60% of the molar amount of the pantoate racemate. In this embodiment, the nopinylammonium L-pantoate also precipitates almost quantitatively, so that the sodium D-pantoate solution which remains can be worked up more easily, because of its lower amine content.

The advantages of (−)-nopinylamine reside not only in the actual resolution of the racemate but also in the fact that it can readily be re-purified by distillation and that, unexpectedly, its configuration is stable.

EXAMPLE 1

(−)-Nopinylamine 138 g (1mole) of nopinone were exposed to a hydrogen pressure of 100 bars, in the presence of 170 g (10 moles) of ammonia, 20 g of Raney nickel and 200 ml of methanol, for 6 hours at 90° C.

The conventional working up of the liquid phase by distillation gave (−)-nopinylamine in 93% yield. Boiling point = 76° C/11 mm Hg, $[\alpha]_D = -20.3°$.

Nopinone was prepared by ozonolysis of (−)-β-pinene at from −5° to −10° C in methanol solution, followed by reduction of the peroxide intermediate compound with zinc/acetic acid. Yield: 94%, boiling point = 95° C/16 mm Hg.

EXAMPLE 2

(−)-N,N-Dimethylnopinylamine

This compound was prepared by the method described in Example 1, with dimethylamine instead of ammonia. Yield: 85%, boiling point = 82° C/13 mm Hg, $[\alpha]_D = -3.3°$ (1% strength in ethanol).

EXAMPLE 3

(−)-N-Methylnopinylamine

Using the method indicated in Example 1, but with methylamine as the amine component, Raney cobalt as the hydrogenation catalyst and a hydrogen pressure of 200 bars, (−)-N-methylnopinylamine is obtained in 90% yield. Boiling point = 93° C/22 mm Hg, $[\alpha]_D = -33.5°$.

EXAMPLE 4

26 g (0.2 mole) of DL-pantolactone were first saponified in a solution of 70 ml of water and 8 g of sodium hydroxide (0.2 mole) and a solution of 17.5 g (0.1 mole) of (−)-nopinylamine hydrochloride and 90 ml of water was then added at 50° C. On cooling gradually, whilst stirring, a white precipitate of (−)-nopinylammonium L-pantoate was formed in the course of 2 hours. The precipitate was separated off and washed with twice 30 ml of ice water.

The combined filtrates were rendered alkaline with a few drops of sodium hydroxide solution, extracted with ether to remove traces of the nopinylamine liberated, and then brought to pH 1 with concentrated sulfuric acid. This resulted in the re-conversion of D-pantoic acid to D-pantolactone, which was extracted from the aqueous phase with methylene chloride and recrystallized, as the pure enantiomer, from diisopropyl ether; yield: 82%.

The crystalline nopinylammonium L-pantoate was converted analogously to L-pantolactone, which can be racemized by conventional methods and recycled to the resolution process.

The (−)-nopinylamine was also recoverable, virtually quantitatively, by conventional methods.

If 50% strength aqueous methanol was used instead of water as the crystallization medium for (−)-nopinylammonium L-pantoate, but in other respects the method described above was employed, a yield of D-pantolactone of 84% was achieved.

We claim:

1. Nopinylamines of the general formula I

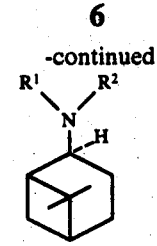

I

-continued

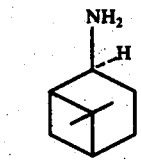

where $R^1$ and $R^2$ are identical or different and are hydrogen or alkyl of 1 to 5 carbon atoms, and the salts of these amines with mineral acids and with alkylcarboxylic acids of 1 to 4 carbon atoms.

2. Nopinylamine of the formula

* * * * *